United States Patent [19]

Cinberg et al.

[11] Patent Number: 5,178,623
[45] Date of Patent: Jan. 12, 1993

[54] TYMPANIC VENTILATION TUBE, APPLICATOR, AND RELATED TECHNIQUE

[76] Inventors: James Z. Cinberg, 167 N. Ridgewood Rd., South Orange, N.J. 07079; Peter J. Wilk, 185 W. End Ave., New York, N.Y. 10023

[21] Appl. No.: 833,511

[22] Filed: Feb. 11, 1992

[51] Int. Cl.$^5$ .............................................. A61F 17/00
[52] U.S. Cl. ...................................... 606/109; 606/1; 606/108; 606/167; 606/170
[58] Field of Search .................... 606/108, 109, 1, 167, 606/170, 180; 623/10; 604/264

[56] References Cited

U.S. PATENT DOCUMENTS

| | | | |
|---|---|---|---|
| 3,530,860 | 9/1970 | Majoros | 606/109 |
| 3,871,380 | 3/1975 | Heros | 604/264 |
| 3,888,258 | 6/1975 | Akiyama | 606/109 |
| 3,948,271 | 4/1976 | Akiyama | 606/109 |
| 3,982,545 | 9/1976 | Silverstein | 604/264 |
| 4,168,697 | 9/1979 | Cantekin | 604/264 |
| 4,764,168 | 8/1988 | Suh | 604/264 |
| 4,775,370 | 10/1988 | Berry | 604/264 |
| 5,026,378 | 6/1991 | Goldsmith | 606/109 |
| 5,047,053 | 9/1991 | Jahn | 623/10 |

FOREIGN PATENT DOCUMENTS 1326276  7/1987  U.S.S.R. .............................. 606/109

*Primary Examiner*—Stephen C. Pellegrino
*Assistant Examiner*—Glenn K. Dawson
*Attorney, Agent, or Firm*—R. Neil Sudol; Henry D. Coleman

[57] ABSTRACT

A tympanic ventilation tube device for use in incising an ear drum and ensuring continued drainage of fluid from the middle ear comprises a tube, a first flange connected to one end of the tube, and a second flange connected to an opposite end of the tube, the first flange being provided with a cutting edge. The cutting edge includes a pair of straight edge segments oriented at an acute angle to one another to form a cutting wedge extending away from the second flange. A graspable extension is connected to the second flange and projects therefrom on a side thereof opposite the first flange. The ventilation tube is installed by using an elongate applicator rod or obturator releasably coupled to the tube. The rod is made of a material such as a metal or alloy having a limited malleability. Accordingly, the applicator rod may be reconfigured prior to the application of the ventilation tube, thereby facilitating the insertion of the tube at an appropriate position in the tympanic membrane. The applicator rod is joined to the ventilation tube by having a distal end detachably inserted into a proximal end of the tube.

21 Claims, 1 Drawing Sheet

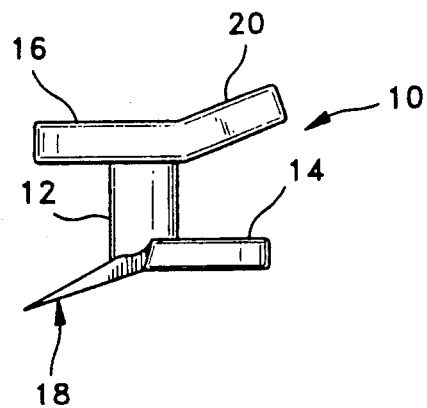
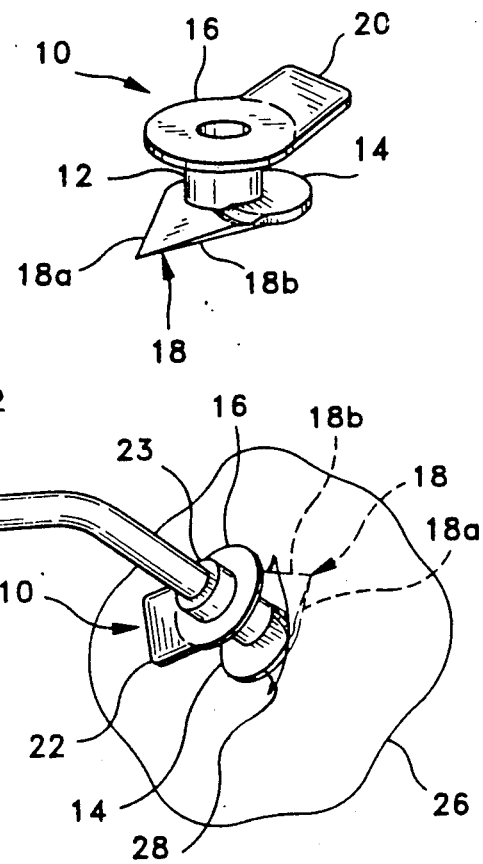
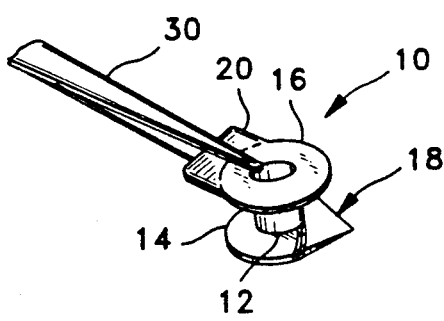
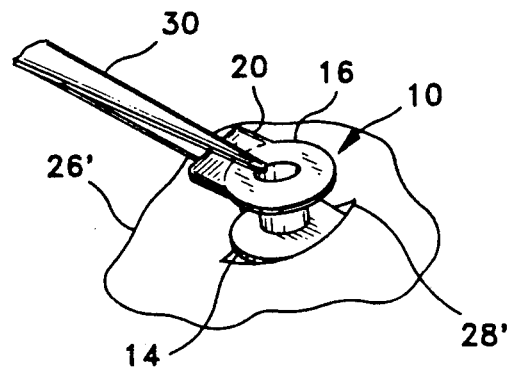

TYMPANIC VENTILATION TUBE, APPLICATOR, AND RELATED TECHNIQUE

BACKGROUND OF THE INVENTION

This invention relates to a ventilation tube for seating in a patient's tympanic membrane for purposes of pressure equalization. This invention also relates to an applicator for use in seating the ventilation tube in the tympanic membrane. In addition, this invention relates to an associated surgical technique.

Children frequently suffer from fluid in the middle ear. A myringotomy or tympanostomy is a surgical operation performed on the ear drum to drain the fluid and ventilate the middle ear for a period longer than would occur with only an incision of the ear drum and subsequent spontaneous drum closure in the week or two after the incision, which occurs as a result of standard repair processes of an incised ear drum. During a myringotomy and tube placement, as conventionally performed, an ear knife cuts the ear drum and creates a small incision. Subsequently, in a second step of the procedure, a ventilation tube is inserted through the incision and manipulated to remain seated via the incision, thereby providing a duct or channel for draining fluid from the middle ear and ventilating the middle ear space via the external auditory canal.

During insertion down into the external auditory canal and seating in the tympanic membrane, the ventilation tube is held by a special grasping forceps. Because the ventilation tube is so tiny and the ear drum so delicate, a myringotomy and tube placement is an especially sensitive operation and gives rise to considerable challenges to a surgeon's dexterity and patience.

OBJECTS OF THE INVENTION

An object of the present invention is to provide an improved ventilation tube for use in draining fluid from the middle ear.

A related object of the present invention is to provide an improved method for performing a myringotomy.

A further object of the present invention is to provide an applicator for facilitating a myringotomy.

An associated object of the present invention is to provide an applicator for facilitating seating of a pressure equalization or ventilation tube in a tympanic membrane.

Another, more particular, object of the present invention is to provide a myringotomy method which is easier and quicker than conventional procedures.

Yet another particular object of the present invention is to provide a ventilation tube which facilitates the myringotomy procedure, thereby reducing the time and costs of the traditional two step method (ear drum incision and tube placement) to an efficient and cost-effective one-step approach.

An even more particular object of the present invention is to provide an implant that can both incise the ear drum and serve as a pressure equalization device.

SUMMARY OF THE INVENTION

A ventilation tube device for releasing fluid from the middle ear comprises, in accordance with the present invention, a tubular member, a first flange connected to one end of the tubular member, and a second flange connected to an opposite end of the tubular member, the first flange being provided with a cutting edge.

Preferably, the cutting edge extends from the first flange in a direction away from the second flange. Also, the cutting edge preferably includes a pair of straight edges oriented at an acute angle to one another to form a cutting wedge.

According to another feature of the present invention, a tongue extension is connected to the second flange. The extension preferably projects from the second flange on a side thereof opposite the first flange.

Pursuant to another feature of the present invention, an elongate applicator member is releasably coupled to the tube. The applicator member may be a rod or tube made of a material such as a metal or alloy having a limited malleability. Accordingly, the applicator member or obturator (whether a tube or a rod) may be reconfigured prior to the application of the tympanic ventilation tube, thereby facilitating the insertion of the tube at an appropriate position in the tympanic membrane.

The applicator rod may be joined to the ventilation tube by having a distal end detachably inserted into a proximal end of the tube.

Generally, the pressure equalization or ventilation tube is approximately three millimeters in width, while the flanges are spaced from one another by a distance slightly greater than a tympanic membrane thickness, i.e., by approximately 1.5 millimeters.

According to a different conceptualization of the present invention, a ventilation tube for releasing fluid from the middle ear comprises a tubular member including a first flange connected to one end of the tubular member and a second flange connected to an opposite end of the tubular member. An elongate applicator rod is releasably coupled to the ventilation tube. Thus, an applicator rod may be used for controlling placement of a conventional ventilation tube.

Preferably, the elongate applicator rod is made of a material, e.g., a metal or alloy, having a limited malleability.

A method for releasing fluid from the middle ear comprises the steps of (a) providing a tympanic ventilation tube having a first flange at one end and a second flange at an opposite end, the first flange being provided with a cutting edge, (b) pressing the cutting edge against a tympanic membrane so as to form a perforation in the membrane, and (c) moving the first flange through the perforation, while maintaining the second flange on an outer side of the tympanic membrane, thereby seating the tube in the tympanic membrane.

Pursuant to another feature of the present invention, the method further comprises the step of turning the tube during the step of pressing, thereby cutting the tympanic membrane with the cutting edge of the first flange.

Where the tube includes a tongue extension connected to the second flange, the method further comprises the step of grasping the tongue extension to adjust the position of the tube in the perforation. The tongue extension may be grasped with a forceps.

A myringotomy ventilation tube represents a considerable advance. A myringotomy and tube placement can be performed more quickly and with greater ease, inasmuch as the incision and ventilation tube insertion steps are performed by the same instrumentation, namely, the ventilation tube itself on the distal end of an applicator member. In many instances, the disposition of the ventilation tube is completed in essentially one step, there being no need to adjust the position e.g., with a grasping forceps.

This one step technique in accordance with the present invention results in considerable savings inasmuch as disposable incising lancets are no longer needed. Such lancets are almost universally thrown away after a single operation. Although the ventilation tube in accordance with the invention will be more expensive than a conventional ventilation tube, it is expected that a cost saving will still accrue.

BRIEF DESCRIPTION OF THE DRAWING

FIG. 1 is side elevational view, on a substantially enlarged scale, of an implant or ventilation tube for use in incising an ear drum in a myringotomy operation and for subsequently serving as a pressure equalization device, in accordance with the present invention.

FIG. 2 is a perspective view, on an enlarged scale, of the ventilation tube of FIG. 1.

FIG. 3 is a perspective view, also on an enlarged scale, of the ventilation tube of FIG. 1 connected to the distal end of an applicator rod, in accordance with the present invention.

FIG. 4 is a side elevational view, on an enlarged scale, of the applicator rod of FIG. 3, showing a nose extension for releasably coupling the ventilation tube to the application rod.

FIG. 5 is a perspective view, on an enlarged scale, of the ventilation tube of FIGS. 1-3, showing a grasping forceps holding the ventilation tube.

FIG. 6 is a perspective view, on an enlarged scale, of the ventilation tube and grasping forceps of FIG. 5, showing placement or removal of the ventilation tube from an incision formed in an ear drum, in accordance with the present invention.

DETAILED DESCRIPTION

As illustrated in FIGS. 1 and 2, a ventilation tube 10 for use in performing a myringotomy and subsequent pressure equalization comprises a tubular member 12, a first flange or collar 14 connected to a distal end of the tubular member, and a second flange or collar 16 connected to a proximal end of the tubular member. Distal flange 14 is provided along a distal side, i.e., on a side opposite proximal flange 16, with a cutting edge 18 comprising a pair of straight edge segments 18a and 18b oriented at an acute angle with respect to one another to form a cutting wedge extending in a direction away from proximal flange 16.

Ventilation tube 10 further comprises a non-cutting tongue or extension 20 connected to proximal flange 16. Tongue extension 20 projects at a shallow angle from proximal flange 16 on a side thereof opposite distal flange 14.

As depicted in FIG. 3, an elongate applicator rod or obturator 22 is removably coupled to ventilation tube 10 prior to the commencement of a myringotomy. As illustrated in FIG. 4, applicator rod 22 is formed at a distal end with a collar 23 and a distally extending nose portion 24 for releasably holding ventilation tube 10. Nose portion 24 may be inserted into ventilation tube 10 in a loose friction fit.

Applicator rod 22 is made of a material such as a metal or alloy having a limited malleability. Thus, applicator rod 22 may be bent, as shown in FIG. 3, for example, to assume a different configuration prior to the insertion of the rod and ventilation tube 10 into the external auditory canal of a patient. The malleability of applicator rod 22 facilitates the disposition of ventilation tube 10 at an appropriate place in the patient's tympanic membrane.

Ventilation tube 10 can have different dimensions and still be effective for seating in a patient's tympanic membrane. In one configuration, flanges 14 and 16 are approximately three millimeters in diameter, while tubular member 12 has an inner diameter of approximately 1.25 millimeters. Flanges 14 and 16 are spaced from one another by a distance approximately equal to the thickness of a tympanic membrane, for example, approximately 1.55 millimeters.

It is to be noted that applicator rod 22 may be used with conventional ventilation tubes, for example, tubes with flanges or collars, but without cutting edge 18 or tongue extension 20. In such a case, the incision in the patient's tympanic membrane is formed conventionally, with a lancet prior to the insertion of the ventilation tube.

In using tympanic ventilation tube 10 and applicator rod 22, ventilation tube 10 is first mounted to the distal end of applicator rod 22. Applicator rod 22 is then manipulated to insert ventilation tube 10 through the patient's auditory canal and to press cutting edge 18 against the tympanic membrane 26 (FIG. 3) so as to form a perforation or incision 28 (FIG. 3) therein. Preferably, upon achieving contact between ventilation tube 10 and the tympanic membrane, applicator rod 22 and concomitantly ventilation tube 10 are twisted or turned to facilitate the penetration of the tympanic membrane by cutting edge 18.

Upon penetration of cutting edge 18 through the tympanic membrane 26 to form perforation 28, applicator rod 22 is manipulated to insert distal flange 14 through the perforation, while maintaining proximal flange 16 on the outside of the tympanic membrane. Upon the seating of ventilation tube 10 so that distal flange 14 and proximal flange 16 are disposed on opposite sides of the tympanic membrane, nose portion 24 of applicator rod 22 is removed from ventilation tube 10.

It is to be noted that ventilation tube 10 may be inserted with instrumentation other than applicator rod 22. For example, as depicted in FIGS. 5 and 6, a grasping forceps 30 may be used to press ventilation tube 10 against tympanic membrane 26', to incise perforation 28', to insert distal flange 14 through the perforation or incision, and to seat ventilation tube 10 in the incision. Alternatively, another instrument (not illustrated) which may be used to perform these steps has an inner tube with a distal end insertable into tubular member 12 and further has an outer tube coaxially surrounding the inner tube and slidable in a distal direction with respect thereto to eject ventilation tube 10 from the distal end of the inner tube upon seating of the ventilation tube in the ear drum.

Although the invention has been described in terms of particular embodiments and applications, one of ordinary skill in the art, in light of this teaching, can generate additional embodiments and modifications without departing from the spirit of or exceeding the scope of the claimed invention. For example, cutting edge 18 may take different forms equivalent to linear segments 18a and 18b, such as an arcuate cutting edge extending through a substantial angle, such as 180°. Accordingly, it is to be understood that the drawings and descriptions herein are profferred by way of example to facilitate comprehension of the invention and should not be construed to limit the scope thereof.

What is claimed is:

1. A tympanic ventilation tube apparatus for releasing fluid from the middle ear comprising:
   a tubular member;
   a first flange connected to one end of said tubular member; and
   a second flange connected to an opposite end of said tubular member, said first flange being provided with a cutting edge said cutting edge facilitating the incising of the tympanic membrane during the insertion of the tubular member, wherein said first flange and said second flange seat against opposite sides of the membrane following said insertion.

2. The apparatus defined in claim 1 wherein said cutting edge extends from said first flange in a direction away from said second flange.

3. The apparatus defined in claim 2 wherein said cutting edge includes a straight edge.

4. The apparatus defined in claim 2 wherein said cutting edge includes a pair of straight edges oriented at an acute angle to one another to form a cutting wedge.

5. The apparatus defined in claim 1, further comprising a tongue extension connected to said second flange.

6. The apparatus defined in claim 5 wherein said tongue extension projects from said second flange on a side thereof opposite said first flange.

7. The apparatus defined in claim 1, further comprising an elongate applicator member releasably coupled to said tubular member.

8. The apparatus defined in claim 7 wherein said elongate applicator member is a rod made of a material having a limited malleability.

9. The apparatus defined in claim 7 wherein said elongate applicator member is a rod with a distal end detachably insertable into a proximal end of said tubular member.

10. The apparatus defined in claim 1 wherein said second flange has a diameter of approximately 3 millimeters, said first flange being separated from said second flange by approximately 1.5 millimeters.

11. A device for releasing fluid from the middle ear, and an inserter therefor, comprising:
    a tubular member;
    a first flange connected to one end of said tubular member;
    a second flange connected to an opposite end of said tubular member said tubular member having a cutting edge extending laterally from said opposite end; and
    an elongate applicator rod releasably coupled to said tubular member, said elongate applicator rod being made of a material having a limited malleability enabling said rod to be manually reconfigured to facilitate an insertion procedure, said cutting edge facilitating the incising of the tympanic membrane during the insertion of said device with said applicator rod.

12. The device and inserter therefor defined in claim 11 wherein said elongate applicator rod has a distal end detachably inserted into a proximal end of said tubular member.

13. A tympanic ventilation tube for releasing fluid from the middle ear, comprising:
    a tubular member;
    a first flange connected to a proximal end of said tubular member;
    a second flange connected to a distal end of said tubular member; and
    cutting means on said tubular member extending laterally from said distal end thereof said cutting means facilitating the incising of the tympanic membrane during the insertion of the ventilation tube, wherein said first flange and said second flange seat against opposite sides of the membrane following insertion.

14. The tympanic ventilation tube defined in claim 13 wherein said blade member is attached to said second flange.

15. A method for releasing fluid from the middle ear, comprising the steps of:
    providing a tympanic ventilation tube having a first flange at one end and a second flange at an opposite end, said first flange being provided with a cutting edge;
    pressing said cutting edge against a tympanic membrane so as to form a perforation in said membrane; and
    moving said first flange through said perforation, while maintaining said second flange on an outer side of said tympanic membrane, thereby seating said tube in said tympanic membrane.

16. The method defined in claim 15, further comprising the step of turning said tube during said step of pressing, thereby cutting said tympanic membrane with said cutting edge.

17. The method defined in claim 16 wherein said cutting edge includes a pair of straight edges oriented at an acute angle to one another to form a cutting wedge.

18. The method defined in claim 15 wherein said tube includes a tongue extension connected to said second flange, further comprising the step of grasping said tongue extension to adjust the position of said tube in said perforation.

19. The method defined in claim 18 wherein said tongue extension projects from said second flange on a side thereof opposite said first flange.

20. The method defined in claim 15 wherein said steps of pressing and moving comprise the step of manipulating said ventilation tube via an elongate applicator member releasably coupled to said tube.

21. The method defined in claim 20 wherein said elongate applicator member is a rod made of a material having a limited malleability, further comprising the step of bending said rod prior to an insertion, into an auditory canal, of a distal end of said rod and said tube carried on said distal end.

* * * * *